(12) United States Patent
Wurziger et al.

(10) Patent No.: US 7,098,357 B2
(45) Date of Patent: Aug. 29, 2006

(54) METHOD FOR DEHYDRATING ORGANIC COMPOUNDS IN A MICROREACTOR

(75) Inventors: Hanns Wurziger, Darmstadt (DE); Guido Pieper, Mannheim (DE); Norbert Schwesinger, Ilmenau (DE)

(73) Assignee: Merck Patent GmbH, Darmstadt (DE)

( * ) Notice: Subject to any disclaimer, the term of this patent is extended or adjusted under 35 U.S.C. 154(b) by 228 days.

(21) Appl. No.: 10/239,392

(22) PCT Filed: Mar. 1, 2001

(86) PCT No.: PCT/EP01/02300

§ 371 (c)(1),
(2), (4) Date: Jan. 8, 2003

(87) PCT Pub. No.: WO01/70650

PCT Pub. Date: Sep. 27, 2001

(65) Prior Publication Data

US 2004/0049078 A1    Mar. 11, 2004

(30) Foreign Application Priority Data

Mar. 23, 2000  (DE) .................................. 100 14 296

(51) Int. Cl.
*C07C 253/00* (2006.01)
*C07B 43/08* (2006.01)

(52) U.S. Cl. ........................ 558/315; 564/215; 564/253
(58) Field of Classification Search .................. 558/315
See application file for complete search history.

(56) References Cited

FOREIGN PATENT DOCUMENTS

| EP | 0872476 | * | 10/1998 |
| WO | WO 9922857 | * | 5/1999 |

* cited by examiner

*Primary Examiner*—Kamal A. Saeed
(74) *Attorney, Agent, or Firm*—Millen, White, Zelano, Branigan, P.C.

(57) ABSTRACT

The present invention relates to a process for the dehydration of organic compounds to give unsaturated compounds.

34 Claims, No Drawings

METHOD FOR DEHYDRATING ORGANIC COMPOUNDS IN A MICROREACTOR

The present invention relates to a process for the dehydration of organic compounds to give unsaturated compounds.

The dehydration of suitable organic compounds to give unsaturated compounds is a process which is carried out very frequently in the chemical industry and whose considerable importance is also reflected in numerous publications on this subject.

However, the performance of dehydrations of this type on an industrial scale is accompanied by safety problems and dangers. Firstly, use is frequently made of relatively large amounts of highly toxic chemical substances, which in themselves already represent a considerable risk to people and the environment, and secondly the reaction conditions can in many cases only be controlled well with considerable effort.

The object of the present invention is therefore to provide a process for the dehydration of organic compounds to give unsaturated compounds which avoids the above-mentioned disadvantages. In particular, It should be possible to carry out this process in a simple, reproducible manner with increased safety for humans and the environment and with good yields, and the reaction conditions should be very easy to control.

This object is achieved, surprisingly, by the process according to the invention for the dehydration of organic compounds to give unsaturated compounds, in which at least one organic compound in liquid or dissolved form is mixed with at least one dehydrating agent in liquid or dissolved form in at least one microreactor and reacted for a residence time, and the dehydrated compound is, if desired, isolated from the reaction mixture.

Advantage embodiments of the process according to the invention are described in the sub-claims.

In accordance with the invention, individual organic compounds or mixtures of at least two of these compounds can be dehydrated by the claimed process. Preferably, individual organic compounds are employed in the process according to the invention.

For the purposes of the invention, a microreactor is a reactor having a volume of $\leq 1000$ µl in which the liquids and/or solutions are intimately mixed at least once. The volume of the microreactor is preferably $\leq 100$ µl, particularly preferably $\leq 50$ µl.

The microreactor is preferably made from thin silicon structures connected to one another.

The microreactor is preferably a miniaturised flow reactor, particularly preferably a static micromixer. The microreactor is very particularly preferably a static micromixer as described in the patent application having the international publication number WO 96/30113, which is incorporated herein by way of reference and is regarded as part of the disclosure.

A microreactor of this type has small channels in which liquids and/or chemical compounds in the form of solutions are mixed with one another by means of the kinetic energy of the flowing liquids and/or solutions.

The channels of the microreactor preferably have a diameter of from 10 to 1000 µm, particularly preferably from 20 to 800 µm and very particularly preferably from 30 to 400 µm.

The liquids and/or solutions are preferably pumped into the microreactor in such a way that they flow through the latter at a flow rate of from 0.01 µl/min to 100 ml/min, particularly preferably from 1 µl/min to 1 ml/min.

In accordance with the invention, the microreactor is preferably heatable.

In accordance with the invention, the microreactor is preferably connected via an outlet to at least one residence zone, preferably a capillary, very particularly preferably a heatable capillary. After mixing in the microreactor, the liquids and/or solutions are fed into this residence zone or capillary in order to extend their residence time.

For the purposes of the invention, the residence time is the time between mixing of the starting materials and work-up of the resultant reaction solution for analysis or isolation of the desired product(s).

The residence time necessary in the process according to the invention depends on various parameters, such as, for example, the temperature or reactivity of the starting materials. It is possible for the person skilled in the art to match the residence time to these parameters and thus to achieve an optimum course of the reaction.

The residence time of the reaction solution in the system used comprising at least one microreactor and, if desired, a residence zone can be adjusted through the choice of the flow rate of the liquids and/or solutions employed.

The reaction mixture is likewise preferably passed through two or more microreactors connected in series. This achieves an extension of the residence time, even at an increased flow rate, and the dehydration reaction components employed are reacted in such a way that an optimum product yield of the desired dehydrated unsaturated compound(s) is achieved.

In a further preferred embodiment, the reaction mixture is passed through two or more microreactors arranged in parallel in order to increase the throughput.

In another preferred embodiment of the process according to the invention, the number and arrangement of the channels in one or more microreactor(s) are varied in such a way that the residence time is extended, likewise resulting in an optimum yield of the desired dehydrated unsaturated compound(s) at the same time as an increased flow rate.

The residence time of the reaction solution in the microreactor, where appropriate in the microreactor and the residence zone, is preferably $\leq 15$ hours, particularly preferably $\leq 3$ hours, very particularly preferably $\leq 1$ hour.

The process according to the invention can be carried out in a very broad temperature range, which is essentially restricted by the heat resistance of the materials employed for the construction of the microreactor, any residence zone and further constituents, such as, for example, connections and seals, and by the physical properties of the solutions and/or liquids employed. The process according to the invention is preferably carried out at a temperature of from $-100$ to $+250°$ C., particularly preferably from $-78$ to $+150°$ C., very particularly preferably from 0 to $+40°$ C.

The process according to the invention can be carried out either continuously or batchwise. It is preferably carried out continuously.

For carrying out the process according to the invention for the dehydration of organic compounds to give unsaturated compounds, it is necessary that the dehydration reaction be carried out as far as possible in the homogeneous liquid phase containing no or only very small solid particles since otherwise the channels present in the microreactors become blocked.

The course of the dehydration reaction in the process according to the invention can be followed using various analytical methods known to the person skilled in the art and regulated if necessary. The course of the reaction is preferably followed by chromatography, particularly preferably by gas chromatography, for example by GC-MS, and/or by high-pressure liquid chromatography and regulated if necessary.

The course of the reaction is very particularly preferably followed by high-pressure liquid chromatography. Control of the reaction in the process according to the invention is significantly improved compared with known processes.

After the reaction, the dehydrated products are isolated if desired. The dehydrated product(s) is (are) preferably isolated from the reaction mixture by extraction.

Organic compounds which can be employed in the process according to the invention are all organic compounds which are known to the person skilled in the art as substrates for dehydrations and which dehydrate with formation of unsaturated compounds. The organic compounds are preferably selected from aliphatic, aromatic or heteroaromatic alcohols, amides or aldoximes.

For the purposes of the invention, "unsaturated compounds" means that the dehydration results in the formation of an unsaturated organic compound or an increase in the unsaturated character of the compound if the compound is already unsaturated. This thus includes the dehydration of alcohols to give alkenes and of amides or aldoximes to give nitrites.

Aliphatic alcohols, amides or aldoximes which can be employed are all aliphatic compounds from the above-mentioned classes of substance which are known to the person skilled in the art and which are suitable as substrate for dehydrations in which unsaturated compounds are formed. This also includes straight-chain, branched, saturated or unsaturated compounds.

Aromatic alcohols, amides or aldoximes which can be employed are all aromatic compounds from the above-mentioned classes of substance which are known to the person skilled in the art and which are suitable as substrate for dehydrations in which unsaturated compounds are formed. For the purposes of the invention, this thus includes compounds and/or derivatives which have a monocyclic and/or polycyclic homoaromatic basic structure or a corresponding moiety, for example in the form of substituents.

Heteroaromatic alcohols, amides or aldoximes which can be employed are all heteroaromatic compounds from the above-mentioned classes of substance which are known to the person skilled in the art and which are suitable as substrate for dehydrations in which unsaturated compounds are formed and which contain at least one hetero atom. For the purposes of the invention, heteroaromatic compounds include heteroaromatic compounds and/or derivatives thereof which have at least one monocyclic and/or polycyclic heteroaromatic basic structure or a corresponding moiety, for example in the form of substituents. Heteroaromatic basic structures or moieties preferably contain at least one oxygen, nitrogen or sulfur atom.

Dehydrating agents which can be employed in the process according to the invention are all dehydrating agents which are known to the person skilled in the art and which are suitable for the dehydration of organic compounds to give unsaturated compounds, or mixtures of at least two components. Preferably, a single dehydrating agent is employed in each case in the process according to the invention.

In a further preferred embodiment, the dehydrating agent is at least one compound selected from acids, acid anhydrides, acid halides, carbodiimides or cyanoformates, or a mixture of these dehydrating agents. The acid used is preferably p-toluenesulfonic acid, methanesulfonic acid, trifluoroacetic acid, sulfuric acid, hydrochloric acid, perchloric acid, or a mixture of two or more of these acids. Preferred acid anhydrides are acetic anhydride, trifluoroacetic anhydride, trifluoromethanesulfonic anhydride, or a mixture thereof. Chlorosulfonic acid, chlorosulfonyl isocyanate, acetyl chloride, trichloroacetyl chloride, p-toluenesulfonyl chloride, methanesulfonyl chloride, phosgene, diphosgene, triphosgene, phosphorus oxychloride, phosphorus trichloride, phosphorus tribromide, hexachlorocyclophosphatriazine, thionyl chloride, and mixtures thereof are preferred acid halides. Furthermore, ethyl cyanoformate is a preferred cyanoformate. Examples of preferred carbodiimides include dicyclohexylcarbodiimide, carbonyldiimidazole, and mixtures thereof.

In the process according to the invention, the molar ratio of organic compound employed to dehydrating agent employed depends on the reactivity of the organic compounds employed and the dehydrating agents. The dehydrating agent and the organic compound are preferably used in an equimolar ratio. In a further preferred embodiment, the dehydrating agent is employed in a 1.3-fold to 10-fold molar excess relative to the organic compound, particularly preferably in a 3-fold to 6-fold excess, very particularly preferably in a 4-fold to 5-fold excess.

The selectivity of the reaction depends, besides on the concentration of the reagents employed, on a number of further parameters, such as, for example, the temperature, the type of dehydrating agent used or the residence time. It is possible for the person skilled in the art to match the various parameters to the respective dehydration reaction in such a way that the desired dehydrated product(s) is (are) obtained.

It is essential for the process according to the invention that the organic compounds and dehydrating agent employed are either themselves liquid or are in dissolved form. If these compounds are not themselves already in liquid form, they must therefore be dissolved in a suitable solvent before the process according to the invention is carried out. Preferred solvents are halogenated solvents, particularly preferably dichloromethane, chloroform, 1,2-dichloroethane or 1,1,2,2-tetrachloroethane, straight-chain, branched or cyclic paraffins, particularly preferably pentane, hexane, heptane, octane, cyclopentane, cycloheptane or cyclooctane, or straight-chain, branched or cyclic ethers, particularly preferably diethyl ether, methyl tert-butyl ether, tetrahydrofuran or dioxane, aromatic solvents, particularly preferably toluene, xylenes, ligroin or phenyl ether, N-containing heterocyclic solvents, particularly preferably N-methylpyrrolidone, or mixtures of these solvents.

In the process according to the invention, the danger to people and the environment due to released chemicals is considerably reduced and thus results in increased safety during handling of hazardous materials. The dehydration of organic compounds by the process according to the invention furthermore enables better control of the reaction conditions, such as, for example, reaction duration and reaction temperature, than is possible in the conventional processes. The temperature can be selected individually and kept constant in each volume unit of the system. The course of the dehydration reaction in the reduction can be regulated very quickly and precisely in the process according to the invention. The dehydrated unsaturated products can thus be obtained in very good and reproducible yields.

It is also particularly advantageous that the process according to the invention can be carried out continuously. This makes it faster and less expensive compared with conventional processes, and it is possible to prepare any desired amounts of the dehydrated unsaturated compounds without major measurement and control effort.

The invention is explained below with reference to an example. This example serves merely to explain the invention and does not restrict the general inventive idea.

EXAMPLES

Dehydration of Benzaldoxime to Benzonitrile

The dehydration of benzaldoxime using methanesulfonyl chloride was carried out in a static micromixer (Technical University of Ilmenau, Faculty of Machine Construction, Dr.-Ing. Norbert Schwesinger, PO Box 100565, D-98684, Ilmenau) having a physical size of 40 mm×25 mm×1 mm and having a total of 11 mixing stages with a volume of 0.125 µl each. The total pressure loss was about 1000 Pa.

The static micromixer was connected via an outlet and an Omnifit medium-pressure HPLC connector (Omnifit, Great Britain) to a Teflon capillary having an internal diameter of 0.49 mm and a length of 1.0 m. The reaction was carried out at room temperature.

A 2 ml disposable injection syringe was filled with part of a solution of 1.0 g (8 mmol) of benzaldoxime and 8 ml of N-methylpyrrolidone, and a further 2 ml syringe was filled with part of a solution of 1.4 g (12 mmol) of methanesulfonyl chloride in 8 ml of N-methylpyrrolidone. The contents of the two syringes were subsequently transferred into the static micromixer by means of a metering pump (Harvard Apparatus Inc., Pump 22, South Natick, Mass., USA). Before performance of the reaction, the experimental arrangement was calibrated with respect to the dependence of the residence time on the pump flow rate. The residence time was set to 3.75 minutes. The reactions were followed with the aid of a Merck Hitachi LaChrom HPLC instrument. The temperature of the static micromixer and the Teflon capillary were controlled in a jacketed vessel thermostatted at 150° C.

For a reaction duration of 3.75 minutes, complete conversion of the benzaldoxime exclusively into benzonitrile was observed.

What is claimed is:

1. A process for dehydration of an organic compound to obtain the corresponding unsaturated compound said process comprising:
    mixing at least one organic compound in liquid or dissolved form with at least one dehydrating reagent in liquid or dissolved form in at least one microreactor, and
    reacting said at least one organic compound and said at least one dehydrating reagent therein for a sufficient time to obtain the corresponding unsaturated compound, and
    optionally isolating the corresponding unsaturated compound from the reaction mixture,
    wherein said at least one organic compounds is selected from aliphatic alcohols, aromatic alcohols, heteroaromatic alcohols, aliphatic amides, aromatic amides, heteroaromatic amides, aliphatic aldoximes, aromatic aldoximes, and heteroaromatic aldoximes, and
    said at least one dehydrating agent is selected from acids, acid anhydrides, acid halides, carbodiimides and cyanoformates.

2. A process according to claim 1, wherein the microreactor is a miniaturized flow reactor.

3. A process according to claim 1, wherein the microreactor is a static micromixer.

4. A process according to claim 1, wherein the microreactor is connected via an outlet to a capillary.

5. A process according to claim 1, wherein the volume of the microreactor is ≦100 µl.

6. A process according to claim 1, wherein the microreactor is heatable.

7. A process according to claim 1, wherein the microreactor has channels which have a diameter of from 10 to 1000 µm.

8. A process according to claim 1, wherein the reaction mixture flows through the microreactor at a flow rate of from 0.01 µl/min to 100 ml/min.

9. A process according to claim 1, wherein the residence time of the compounds employed in the microreactor is ≦15 hours.

10. A process according to claim 1, wherein said process is carried out at a temperature of from −100 to +250° C., preferably from −78 to +150° C., particularly preferably from 0 to +40° C.

11. A process according to claim 1, the course of the reaction is followed by chromatography and optionally regulated.

12. A process according to claim 1, wherein said at least one dehydrating agent is an acid selected from p-toluenesulfonic acid, methanesulfonic acid, trifluoroacetic acid, sulfuric acid, hydrochloric acid, perchloric acid, and mixtures thereof.

13. A process according to claim 1, wherein said at least one dehydrating agent is an acid anhydride selected from acetic anhydride, trifluoroacetic anhydride, trifluoromethanesulfonic anhydride, and mixtures thereof.

14. A process according to claim 1, wherein said at least one dehydrating agent is an acid halide selected from chlorosulfonic acid, chlorosulfonyl isocyanate, acetyl chloride, trichloroacetyl chloride, p-toluenesulfonyl chloride, methanesulfonyl chloride, phosgene, diphosgene, triphosgene, phosphorus oxychloride, phosphorus trichloride, phosphorus tribromide, hexachlorocyclophosphatriazine, thionyl chloride, and mixtures thereof.

15. A process according to claim 1, wherein said at least one dehydrating agent is ethyl cyanoformate.

16. A process according to claim 1, wherein said at least one dehydrating agent is a carbodiimide selected from dicyclohexylcarbodiimide, carbonyldiimidazole, and mixtures thereof.

17. A process according to claim 1, wherein the dehydrating agent is employed in an equimolar ratio.

18. A process according to claim 4, wherein the capillary is a heatable capillary.

19. A process according to claim 5, wherein the volume of the microreactor is ≦50 µl.

20. A process according to claim 7, wherein said channels have a diameter of from 20 to 800 µm.

21. A process according to claim 20, wherein said channels have a diameter of from 30 to 400 µm.

22. A process according to claim 8, wherein the reaction mixture flows through the microreactor at a flow rate of from 1 µl/min to 1 ml/min.

23. A process according to claim 9, wherein the residence time of the compounds employed in the microreactor is ≦1 hour.

24. A process according to claim 10, wherein said process is carried out at a temperature of from −78 to +150° C.

25. A process according to claim 24, wherein said process is carried out at a temperature of from 0 to +40° C.

26. A process according to claim 1, wherein the dehydrating agent is employed in a 1.3-fold to 10-fold molar excess relative to the organic compound.

27. A process according to claim 26, wherein the dehydrating agent is employed in a 3-fold to 6-fold molar excess relative to the organic compound.

28. A process according to claim 27, wherein the dehydrating agent is employed in a 4-fold to 5-fold molar excess relative to the organic compound.

29. A process according to claim 1, wherein said at least one dehydrating agent is selected from p-toluenesulfonic acid, methanesulfonic acid, trifluoroacetic acid, sulfuric acid, hydrochloric acid, perchloric acid, acetic anhydride, trifluoroacetic anhydride, trifluoromethanesulfonic anhydride, chlorosulfonic acid, chlorosulfonyl isocyanate, acetyl chloride, trichloroacetyl chloride, p-toluenesulfonyl chloride, methanesulfonyl chloride, phosgene, diphosgene, triphosgene, phosphorus oxychloride, phosphorus trichloride, phosphorus tribromide, hexachlorocyclophosphatriazine, thionyl chloride, ethyl cyanoformate, dicyclo-hexylcarbodiimide, and carbonyldiimidazole.

30. A process according to claim 1, wherein said at least one organic compound and said at least one dehydrating agent are dissolved in a solvent selected from halogenated solvents, straight-chain paraffins, branched paraffins, cyclic paraffins, straight-chain ethers, branched ethers, cyclic ethers, aromatic solvents, N-containing heterocyclic solvents, or mixtures thereof.

31. A process according to claim 30, wherein said at least one organic compound and said at least one dehydrating agent are dissolved in a solvent selected from dichloromethane, chloroform, 1,2-dichloroethane, 1,1,2,2-tetrachloroethane, pentane, hexane, heptane, octane, cyclopentane, cycloheptane, cyclooctane, diethyl ether, methyl tert-butyl ether, tetrahydrofuran, dioxane, toluene, xylenes, ligroin, phenyl ether, N-methylpyrrolidone, or mixtures thereof.

32. A process according to claim 29, wherein said at least one organic compound and said at least one dehydrating agent are dissolved in a solvent selected from halogenated solvents, straight-chain paraffins, branched paraffins, cyclic paraffins, straight-chain ethers, branched ethers, cyclic ethers, aromatic solvents, N-containing heterocyclic solvents, or mixtures thereof.

33. A process according to claim 32, wherein said at least one organic compound and said at least one dehydrating agent are dissolved in a solvent selected from dichloromethane, chloroform, 1,2-dichloroethane, 1,1,2,2-tetrachloroethane, pentane, hexane, heptane, octane, cyclopentane, cycloheptane, cyclooctane, diethyl ether, methyl tert-butyl ether, tetrahydrofuran, dioxane, toluene, xylenes, ligroin, phenyl ether, N-methylpyrrolidone, or mixtures thereof.

34. A process according to claim 1, wherein said at least one organic compound is benzaldoxime and said at least one dehydrating agent is methanesulfonyl chloride.

* * * * *